United States Patent
Wu (10) Patent No.: US 10,342,738 B2
(45) Date of Patent: Jul. 9, 2019

(54) MEDICAL METERING DEVICE

(71) Applicant: Biogen MA Inc., Cambridge, MA (US)

(72) Inventor: Haiming Wu, Weston, MA (US)

(73) Assignee: BIOGEN MA, INC., Cambridge, MA (US)

(*) Notice: Subject to any disclaimer, the term of this patent is extended or adjusted under 35 U.S.C. 154(b) by 372 days.

(21) Appl. No.: 15/408,831

(22) Filed: Jan. 18, 2017

(65) Prior Publication Data

US 2017/0202743 A1    Jul. 20, 2017

Related U.S. Application Data

(60) Provisional application No. 62/280,410, filed on Jan. 19, 2016.

(51) Int. Cl.
| | |
|---|---|
| *A61M 5/24* | (2006.01) |
| *A61J 1/20* | (2006.01) |
| *A61J 1/22* | (2006.01) |
| *A61M 5/28* | (2006.01) |
| *A61M 39/24* | (2006.01) |
| *A61M 39/10* | (2006.01) |

(52) U.S. Cl.
CPC ........... *A61J 1/2096* (2013.01); *A61J 1/2003* (2015.05); *A61J 1/22* (2013.01); *A61M 5/2448* (2013.01); *A61M 5/284* (2013.01); *A61M 39/24* (2013.01); *A61J 1/201* (2015.05); *A61J 1/2075* (2015.05); *A61M 2039/1077* (2013.01)

(58) Field of Classification Search
CPC .......... A61J 1/2096; A61J 1/2003; A61J 1/22; A61J 1/2075; A61J 1/201; A61M 39/24; A61M 5/2448; A61M 5/284; A61M 2039/1077
See application file for complete search history.

(56) References Cited

U.S. PATENT DOCUMENTS 2,609,818 A    9/1952  Parrine
3,040,743 A    6/1962  Naess
(Continued)

FOREIGN PATENT DOCUMENTS

EP    1391219 A2    2/2004
EP    1391219 A3    5/2004
(Continued)

*Primary Examiner* — Jason K Niesz
(74) *Attorney, Agent, or Firm* — Finnegan, Henderson, Farabow, Garrett & Dunner LLP (57) ABSTRACT

A metering device that improves the aseptic transfer of powder and reconstitution fluid into the metering device for medical use. In some implementations, the metering device comprises a housing, containing a metering chamber that defines a volume. The housing also has a connection portion, an extraction portion, and a metering member in fluid communication with the metering chamber. In other embodiments, the metering device additionally includes a dispensing aid that facilitates the dispensing of powder from a first container into the metering chamber through the connection portion. The connection portion is capable of insertion into a second container that contains fluid, thereby allowing a mixture of powder and fluid to form in the metering chamber. The mixture, then ready for use, is removable from the metering chamber through the extraction portion by an extraction device.

20 Claims, 5 Drawing Sheets

(56) References Cited

U.S. PATENT DOCUMENTS

| | | |
|---|---|---|
| 3,506,006 A | 4/1970 | Lange, Jr. |
| 3,563,373 A | 2/1971 | Paulson |
| 3,892,237 A | 7/1975 | Steiner |
| 4,732,850 A | 3/1988 | Brown et al. |
| 4,779,763 A | 10/1988 | Klawitter |
| 4,861,335 A | 8/1989 | Reynolds |
| 4,958,622 A | 9/1990 | Selenke |
| 5,067,948 A | 11/1991 | Haber et al. |
| 5,334,163 A | 8/1994 | Sinnett |
| 2002/0004643 A1 | 1/2002 | Carmei et al. |
| 2004/0069044 A1 | 4/2004 | Lavi et al. |
| 2004/0112411 A1 | 6/2004 | Boykin et al. |
| 2006/0079834 A1 | 4/2006 | Tennican et al. |
| 2007/0260375 A1 | 11/2007 | Hilton |
| 2010/0241088 A1* | 9/2010 | Ranalletta ............. A61J 1/2089 604/264 |
| 2012/0290225 A1 | 11/2012 | Julian et al. |

FOREIGN PATENT DOCUMENTS

| | | |
|---|---|---|
| WO | WO 94/06690 | 3/1994 |
| WO | WO 2004/112411 A1 | 12/2004 |
| WO | WO 2014/188407 A1 | 11/2014 |

\* cited by examiner

MEDICAL METERING DEVICE

RELATED APPLICATIONS

This application claims the benefit of U.S. Provisional Patent Application No. 62/280,410, filed 19 Jan. 2016, the contents of which are hereby incorporated by reference in its entirety.

BACKGROUND OF THE INVENTION

Field of the Invention

The present disclosure generally relates to a device for mixing precise, predetermined proportions of powder, extracted from a storage source, with fluid to make a mixture. More specifically, and without limitation, the present disclosure relates to improving the aseptic transfer of lyophilized powder and reconstitution fluid into a metering device for medical used herein, the term reconstitution includes mixing a solid phase into a fluid phase resulting in a solution, a suspension, or a colloide.

Description of Related Prior Art

In the administration of medical treatment, patients often receive injections of reconstituted mixtures. A therapeutic mixture is the result of mixing powder, previously altered for preservation and storage, with liquid, thereby returning the powder to its approximate, original state. Drugs, for example, are often packed and stored in powder form in order to preserve their utility. By way of example, ampicillin, an antibiotic commonly used to treat bacterial infections, is commonly stored in powder form because, in liquid form, it has a short shelf life. For this reason, the administration of ampicillin requires dissolving a powder into liquid to form a solution.

Traditionally, to accomplish this mixing, a user—i.e., a health care provider or a patient—uses a syringe to withdraw a diluent (the mixing liquid) from a first container, and deliver the diluent into a second container where the powder is stored. Delivery of the diluent is accomplished by inserting the syringe into the second container. To ensure the diluent mixes completely with the powder, the syringe is ordinarily removed from the second container while the second container is manipulated or shaken to fully reconstitute the powder. Once the powder and diluent are fully incorporated into a solution, the user returns the syringe into the second container. The solution is then extracted from the second container, back into the syringe. Only then is the solution ready for injection into a patient. This cumbersome process suffers from several drawbacks.

For example, in preparing the mixture for injection into the patient, the syringe is the primary vehicle. Before the syringe is ready for injection, it is inserted into and removed from the first container. It is then inserted into and removed from the second container two times, once to inject the diluent and once to remove the mixture. With each step, the risk of contamination increases because the syringe can come into contact with non-sterile surfaces. Such unsanitary conditions could result in serious harm to the patient.

Further, because the traditional process involves introducing diluent into the powder container, the powder container can be used only once. As a result, multiple single-use containers are used to store powder, thereby increasing the complexity of storage and cost, as well as creating waste.

Yet further, the abovementioned process is unavoidable because prior art devices were incapable of drawing powder through the needle's narrow conduit, and into the syringe.

Even further, the abovementioned process suffers from the looping problem, which describes the problem of mixing different strength powders to achieve a specific, prescribed dosage. Traditionally, a powdered drug will have different formulations related to different strengths or potencies. This occurs because treatments differ between patients. Indeed, not each person using the same drug requires the same level of potency. A problem arises, however, when trying to generate a particular drug strength because of how the powder is stored. The potency of a drug is measured by international units ("IU") and is a function of the amount used. A single drug can have several different IUs, each stored in different vials with identifying markings. If a prescription calls for a drug having a specific IU that does not match the IUs stored in the available vials, a user will have to mix powders from varying vials to achieve the prescribed drug. The problem is further complicated because different drug strengths are separated by predetermined intervals that may be inconsistent with the prescribed dosage. So, for example, if a prescription calls for a drug having 120 IU, and the drug is stored in two vials, one having 100 IU and the other having 50 IU, the precise dosage cannot be achieved. The user will therefore have to take a dosage with either a lower or higher potency than the one prescribed. This lessens the efficacy of the treatment.

SUMMARY

The present invention seeks to overcome the abovementioned problems. Accordingly, an object of the present invention is to provide a metering device and process for a simplified, aseptic transfer of powder and reconstitution fluid into the metering device for medical use.

In illustrative embodiments, the metering device comprises a housing, containing a metering chamber that defines a volume. The housing also has a connection portion, an extraction portion, and a metering member that are in fluid communication with, and provide multiple access points to, the metering chamber. Thus, another object of the present invention is allowing a mixture of powder and reconstitution fluid to form in the metering chamber as opposed to a vial, thereby streamlining the reconstitution process.

In other embodiments, the metering device further has, for example, a dispensing aid that facilitates the dispensing of powder into the metering chamber through the connection portion. In this way, powder can be withdrawn from a sterile connection portion, thereby allowing lyophilized powder to be stored in bulk. In some embodiments, the dispensing aid helps to maintain sterility in the transfer of powder by refreshing the metering chamber environment. Thus, another object of the invention is to reduce the need for single-use vials, thereby simplifying the aseptic storage of lyophilized powder.

This feature illustrates that yet another object of the invention is to solve the pooling problem, as described above. The instant invention resolves this problem, by allowing for bulk storage of powder that would otherwise be stored in a plurality of smaller vials. The increased storage capacity enables drug manufacturers to reduce the variance between stored drugs having different IUs, thereby reducing the cost associated with creating a particular formulation and storing it. Further, a precise dosage with a particular IU can be readily achieved because virtually any amount can be dispensed from bulk storage. In this way, the exact potency corresponding to a particular prescription can be achieved without mixing between vials of various sizes or dosages.

During use of an exemplary embodiment of the present invention, powder from a first container is drawn into the metering chamber through the connection portion. The connection portion is then inserted into a second container that contains a reconstitution fluid thereby allowing a mixture to form in the metering chamber. The mixture, then ready for injection, is removed from the metering chamber through the extraction portion. As demonstrated by this unique a process, yet another object of the invention is to reduce the steps necessary to form a sterile reconstituted mixture, thereby reducing the risk of contamination and, thus, minimizing the risk of harm to the patient.

Other embodiments of this disclosure are disclosed in the accompanying drawings, description, and claims. Thus, this summary is exemplary only, and is not to be considered restrictive.

BRIEF DESCRIPTION OF DRAWINGS

The accompanying drawings, which are incorporated in and constitute part of this specification, and together with the description, illustrate and serve to explain the principles of various exemplary embodiments.

DETAILED DESCRIPTION OF EXEMPLARY EMBODIMENTS

The claimed subject matter is described with reference to the drawings, wherein like reference numerals are used to refer to like elements throughout. In the following description, for purposes of explanation, numerous specific details are set forth in order to provide a thorough understanding of the subject innovation. It may be evident, however, that the claimed subject matter may be practiced without these specific details. In other instances, well-known structures and devices are shown in block diagram form in order to facilitate describing the subject innovation. Moreover, it is to be appreciated that the drawings may not be to scale. Moreover, the words "exemplary" or "illustrative" are used herein to mean serving as an example, instance, or illustration. Any aspect or design described herein as "exemplary" or "illustrative" is not necessarily to be construed as preferred or advantageous over other aspects or designs.

The present invention involves a metering device 10 for medical use. In an exemplary embodiment, the metering device 10 is an assembly that includes a housing 20, a dispensing aid 80, and an extraction device 90. The metering device 10 can be made of glass or plastic, or of any other material suitable for use in accordance with the present disclosure.

Figure 1:
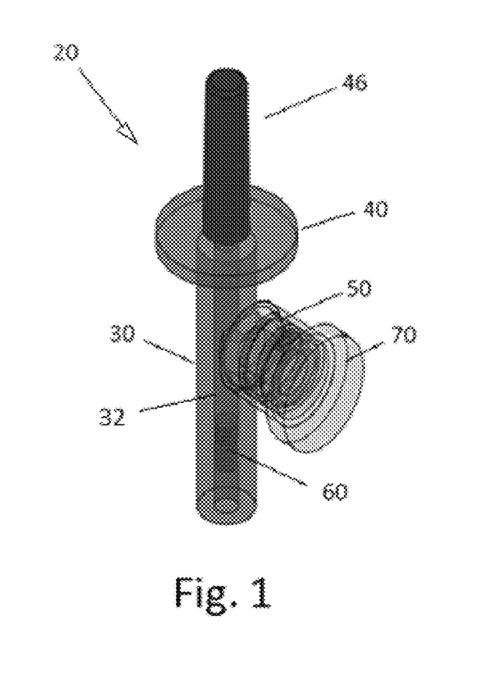
FIG. 1 depicts an exemplary housing according to the present disclosure.

In an exemplary embodiments shown in FIG. 1, the housing 20 includes a metering chamber 30, connection portion 40, and extraction portion 50. The metering chamber, connection portion 40, and extraction portion 50 are in fluid communication with each other, allowing powder and fluid to travel through different portions of the housing 20. The housing 20 can be clear or opaque so that a user can view the contents disposed therein. Housing 20 may further comprise coloring or indicia to enhance the visualization of a powder or fluid moving through the housing.

FIG. 1 further depicts the metering chamber 30 includes a reservoir having a volume for receiving powder and reconstitution fluid. The metering chamber 30 is shown having a generally cylindrical shape with an inner surface 32 having a circular cross-section, but it can also have other cross-sectional shapes, such as, for example, square, rectangular, trapezoidal, or frusto-conical. Distal boundaries of the metering chamber are defined on opposite ends by the connection portion 40 and a metering member 60 respectively. As discussed in further detail below, the metering member 60 is configured to adjust the volume of the metering chamber 30. The metering member 60 is disposed within the metering chamber 30 and contacts the inner surface 32 of the metering chamber 30 in a sealing engagement. In this way, it creates a boundary of the metering chamber 30 so as to define a volume of the metering chamber 30. In the exemplary embodiment of FIG. 6, the metering chamber 30 is shown having a fixed volume with the extraction portion 50 disposed at a distal end of the metering chamber 30. The extraction portion 50 can be covered by plug 70 that comprises, for example, an overmold closure capable of being pierced by an extraction device 90 to allow for the extraction of reconstitution fluid air, powder, or mixtures thereof from the metering chamber 30.

Further, in some embodiments, the metering chamber 30 may have one or more vents (not shown) for alleviating pressure, especially when the metering chamber is pre-filled with a protective gas for sterility. The vent can be disposed at any position on the metering chamber 30, or the extraction portion 50 can be used a vent. Alternatively, in some embodiments, the connection portion 40 has a broad opening that can provide a venting means for the metering chamber 30.

Figure 4:
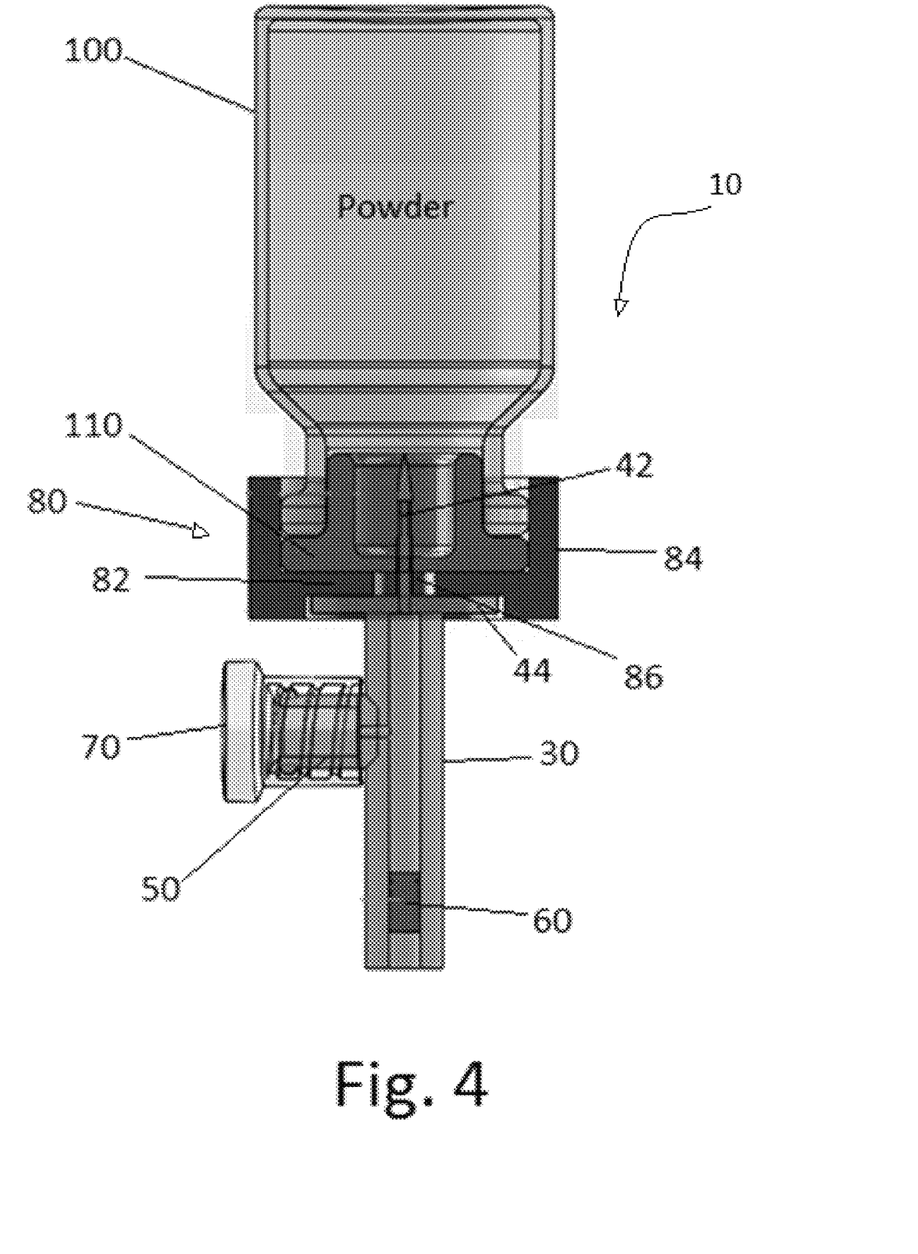
FIG. 4 depicts an exemplary assembly of the housing of FIG. 1 and dispensing aid of FIG. 2 in use according to the present disclosure.

In the exemplary embodiment shown in FIG. 4, the connection portion 40 is configured to direct powder and reconstitution fluid into the metering chamber 30. The connection portion 40 includes an end piece 44 and a piercing portion 42. The end piece 44 provides a platform to stabilize a container or the dispensing aid 80 when disposed thereon. In some embodiments, the piercing portion 42 is comprised of a needle, such as, for example, a blunt cannula or a Nokor needle. However, any suitable conduit capable of transferring powder can be used. The piercing portion 42 can be enclosed by a cap 46 in order to maintain a sterile, hazard-free condition prior to use.

FIG. 4 further depicts that the piercing portion 42 is capable of being inserted through a sealed closure 110 of a first container 100 holding powder. As is common with the storage of sterile material for medical use, the first container 100, in one embodiment, is a vial containing, at its opening, a closure 110 comprised of, for example an elastomer such as rubber, silicon, or other suitable material. For use in accordance with the present invention, the closure 110 need only be capable of being pierced by the piercing portion 42 while maintaining an otherwise sterile environment for the contents therein disposed. Yet further, in FIG. 4, the vial is shown being fully inverted to allow gravity to assist in dispensing, but other configurations have been considered. As discussed in further detail below; after the piercing portion 42 is inserted into the first container 100, the dispensing aid 80 is activated in order to encourage powder, disposed within the first container 100, to pass through the piercing portion 42 into the metering chamber 30. After withdrawing powder from the first container 100, the piercing portion 42 is removed therefrom and inserted into a second container 200 containing a reconstitution fluid, such as, for example, a diluent, a solvent, or an external place for a suspension.

Figure 5:
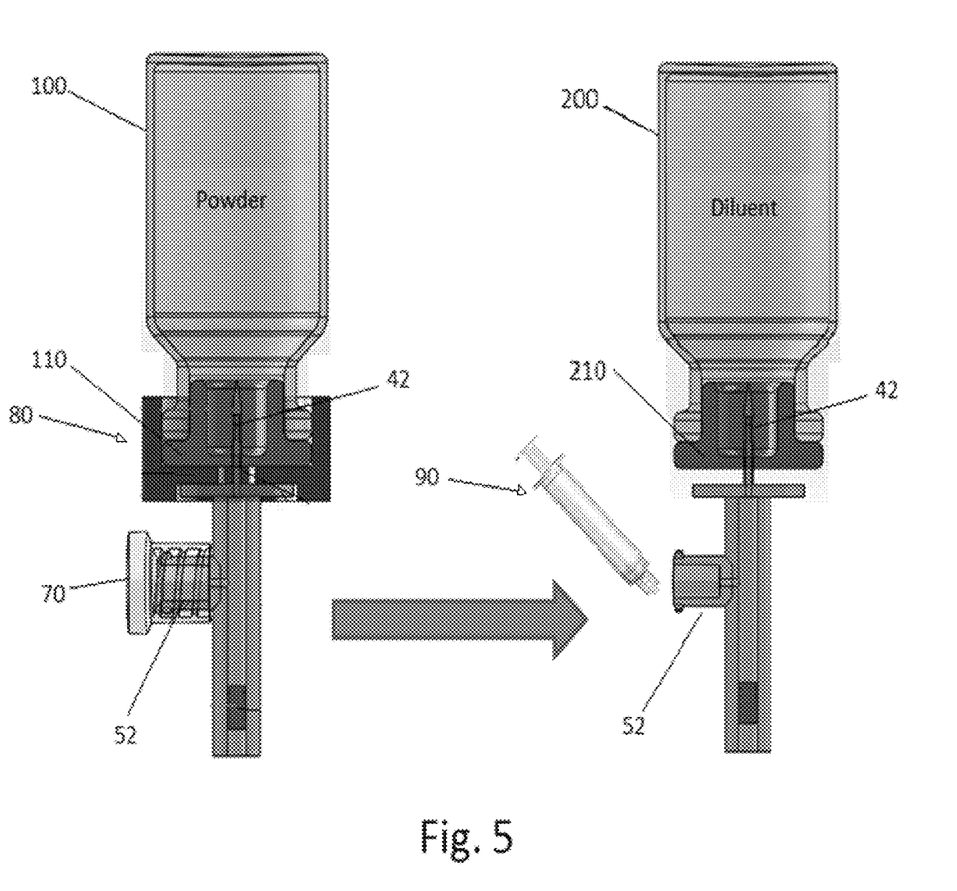
FIG. 5 depicts an exemplary use of the exemplary assembly of FIG. 4 along with the extraction device of FIG. 3 according to the present disclosure.
Figure 6:
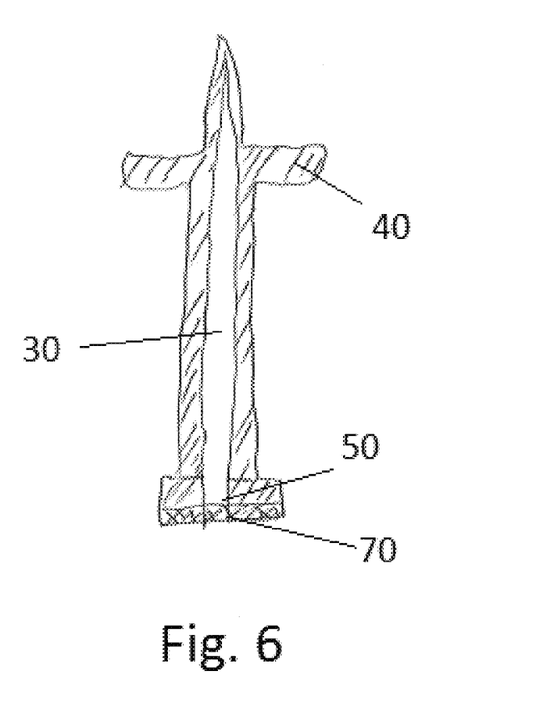
FIG. 6 depicts an alternative embodiment of the metering chamber according to the present disclosure.

FIG. 1, FIG. 4, and FIG. 5 depict an embodiment of the present invention wherein the extraction portion 50 is connected to the housing 20 and is in fluid communication with the metering chamber 30. It provides an outlet for the removal of fluid from the metering chamber 30. In one embodiment, the extraction portion 50 protrudes from the housing 20, for example perpendicular to a longitudinal axis of the metering chamber 30 between the connection portion 40 and the metering member 60. But the extraction portion 50 can be positioned at different locations on the housing 20, and have different configurations. For example, the extraction portion 50 can be disposed at the bottom of the metering chamber 30 as shown in FIG. 6. It can also be disposed on the housing 20 in like manner as the embodiment shown in FIG. 4, but not projecting outwardly from the housing 20. Instead, the extraction portion 50 can comprise an aperture in the metering chamber 30 that is covered by, for example, an over mold closure capable of being pierced by an extraction device 90 to facilitate removal of fluid air, powder, or mixtures thereof from the metering chamber 30. In the embodiment, the extraction portion 50 comprises a port 52 that provides access to the metering chamber 30. The port 52 is configured to receive a plug 70. The connection between the port 52 and plug 70 can be accomplished by a luer taper, though other suitable connecting mechanisms can be used, such as, for example, threads or a snap-fit engagement. The plug 70 can be made, for example, from elastomer, but it can also be formed from thermoplastic such as, for example, polyethylene terephthalate ("PET"). A sealing sponge-like structure may be utilized with any appropriate material.

According to the exemplary embodiment shown in FIG. 1, at least a portion of the metering member 60 is disposed within the metering chamber 30. It sealingly engages the inner surface 32 of the metering chamber 30 in order to act as a boundary. In the embodiment, the metering member 60 is a stopper, movable within the metering chamber 30 to allow a user to adjust the volume of the metering chamber 30. This accommodates a user's need for various, precise doses. To this end, the metering chamber 30 can have marks (not shown) disposed thereon corresponding to different volumes. The metering member 60 can also include, for example, a handle (not shown) extending to an outside of the housing 20 to allow easy adjustment of the metering member 60. In this way, the metering member 60 may have a piston-rod configuration. Additionally, in one embodiment, the metering chamber 30 is flexible and the metering member 60 comprises a clamp or an O-ring configured to provide an adjustable volume of the metering chamber 60. Alternatively, housing 20 could have a surface shaped or modified to improve grip, for example with ribs, bumps, concavities or surface roughening. In an alternative embodiment, the metering member 60 can be selectively fixed by a locking mechanism to avoid accidental movement. The metering member 60 can be fixed, or locked in place, either by a user or, for example, by a pharmacist to prevent inadvertent movement of the metering member. This feature allows a user to measure a precise dosage without risking a change in the metering chamber 30 volume. The metering member may be positionable by virtue of a mechanism such as, for example, a screw thread or a ratcheting connection with the metering chamber or chamber entrance.

Figure 2:
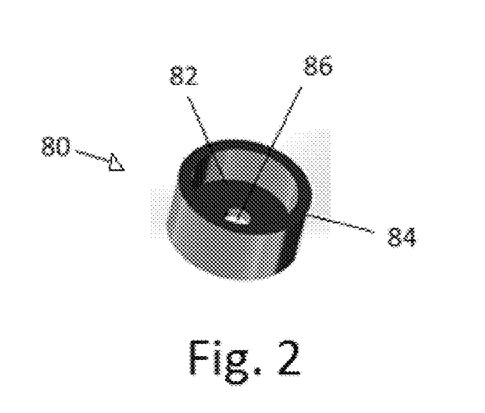
FIG. 2 depicts an exemplary dispensing aid according to the present disclosure.
Figure 7:
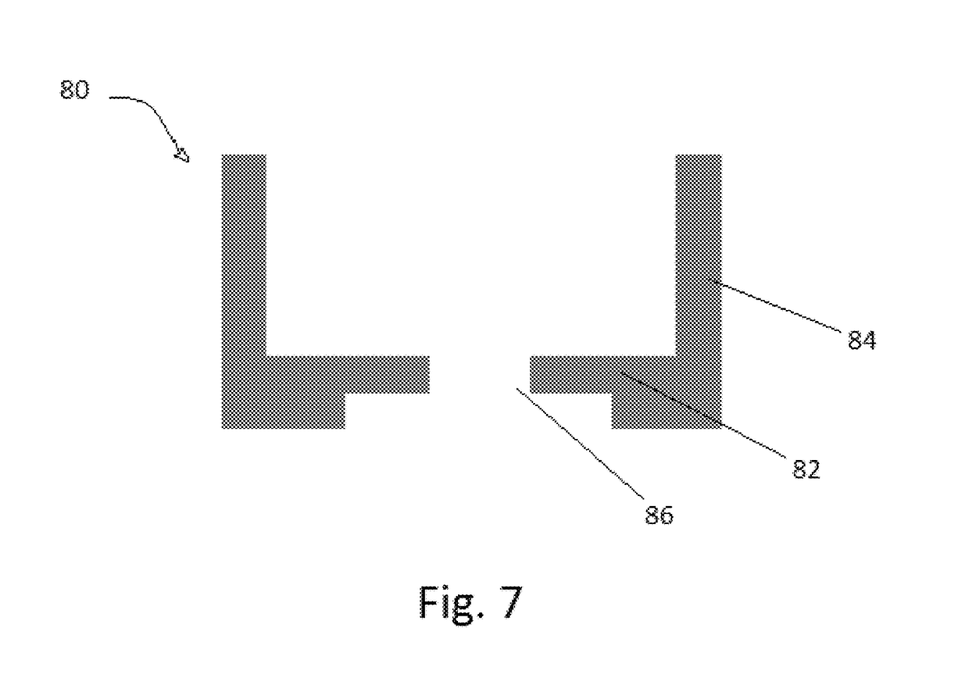
FIG. 7 depicts a cross section of the exemplary dispensing aid of FIG. 2 according to the present disclosure.

FIG. 2 depicts an exemplary embodiment of the dispensing aid 80. FIG. 7 depicts a cross section of the exemplary dispending 80 shown in FIG. 2. The dispensing aid 80 facilitates removal of powder from the first container 100 into the metering chamber 30 through the connection portion 40. In one embodiment, the dispensing aid 80 is configured to surround the connection portion 40. For example, FIG. 4 depicts the dispensing aid 80 having a planar end 82 and an annular rim 84 projecting from, and extending circumferentially around, the planar end 82. The planar end 82 further has an opening 86 disposed in its center through which the piercing portion 42 protrudes. The annular rim secures the dispensing aid 80 to both the first container 100 and the connection portion 40 to prevent the unwarranted dislodgment or removal therefrom. In some instances, annular rim 84 has a recess or a protrusion along at least a portion of the inner wall to allow for a snap fit onto connection portion 40. In some embodiments, annual rim 84 may have at least a portion of a screw thread to mate with connection portion 40. In other embodiments, the attachment between annual rim 84 and connection portion 40 may be a friction fit. Further, planar end 82 and the annular rim 84 cooperate to secure an inverted container in place to allow steady, measured dispensing. However, according to the exemplary embodiment, the dispensing aid 80 is optionally removable from both the connection portion 40 and first container 100. Alternatively, dispensing aid 80 can be fixed to either the connection portion 40 or the first container 100. Additionally, the dispensing aid 80 can have other shapes and configurations in accordance with the present invention. For example, the dispensing aid 80 need not fully encircle the connection portion 40 or the first container 100. It can, for example, have a C-shape or any other shape so long as it is capable of encouraging the dispensing of powder from the first container 100 into the metering chamber 30 through the piercing portion 42.

In the exemplary embodiment shown in FIG. 4, when activated, the dispensing aid 80 encourages powder from the first container 100 to flow into the piercing portion 42, and, further, into the metering chamber 30. Activation of the dispensing aid 80 is necessary because the particulate matter that makes up the powder does not necessarily operate in like manner as a fluid. When housed in an inverted vial and introduced to a piercing device such as a piercing portion 42, for example, the powder may not pass through the piercing portion 42 absent coaxing. The dispensing aid 80 provides such coaxing in a number of different ways.

Figure 8:
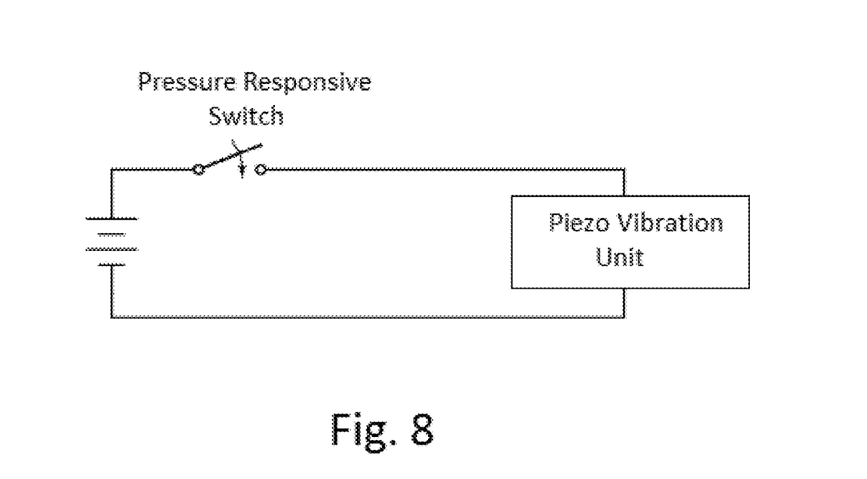
FIG. 8 depicts an exemplary diagram of an automated circuitry of the dispensing aid of FIG. 2 according to the present disclosure.

For instance, in one embodiment, the dispensing aid 80 can be configured to vibrate at an accelerated rate so as to jostle otherwise static powder, encouraging the powder to fall through the piercing portion 42 into the metering chamber 30. This occurs when vibrational and gravitational forces overcome the static, frictional forces that bind particles of powder together, allowing the powder to move more freely. To accomplish the vibration, the dispensing aid 80 can include a battery powered piezoelectric vibration unit that can be activated manually by a button, onboard switch, or remote, or, for example, it can be set to activate automatically when a sensor indicates to a control unit that the piercing portion 42 is inserted into the first container 100. Alternatively, insertion of the piercing portion 42 into the first container 100 could activate the dispensing aid 80 by triggering a button or a pressure sensitive switch, as shown in FIG. 8. Vibration may also be induced mechanically by using, for example, a spring such as a clock spring. The spring may be wound by means of torqueable portions of the dispensing aid or other moveable mechanism. When released, the spring energy may drive a vibrating mechanism, for example a small cantilever or adjacent moveable surfaces having opposing ridges.

In an alternative embodiment, the dispensing aid 80 can comprise a vacuum mechanism to withdraw powder and like substances from the vial. For example, a vacuum or pump can be attached to the metering device via the dispensing aid 80 to create a pressure differential between the metering chamber and the vial, thereby drawing powder into the metering chamber. The vacuum can be attached to one of either the dispensing aid 80 or, alternatively, the extraction portion 50, but in either case, air must be withdrawn from the metering chamber 30 to create a vacuum that draws powder into it.

In yet another embodiment, the dispensing aid 80 can comprise a pressure mechanism to withdraw powder and like substances from the vial. For instance, a protective gas, e.g., nitrogen, can be introduced into the first container 100 containing powder. The increased pressure in the first container 100 forces powder down through the connection portion 40 into the metering chamber 30. The gas can be introduced into the first container 100 through an opening in the dispensing aid 80, but, alternatively, it can be introduced through the extraction portion 50. In the latter case, a co-axial needle would need to be used to allow for two conduits—i.e., one for the protective gas to enter the first container 100, and another for the powder to exit it.

Both of the alternative, exemplary embodiments that use a dispensing aid 80 comprising either a vacuum or a pressure mechanism increase the sterility of powder transfer by refreshing the metering chamber environment while introducing powder into it. This is true because both the presence of a vacuum and the introduction of a protective gas into an enclosed environment enhances its sterility by removing harmful bacteria and contaminants. Thus, when air is removed from the metering chamber 30 to create a vacuum and powder is introduced therein, the air is refreshed and sterility is maintained. Also, when a protective gas is introduced into the first container 100 forcing powder into the metering chamber 30, some amount of protective gas is also introduced into the metering chamber 30, thereby maintaining a sterile environment.

In accordance with an exemplary embodiment shown in FIG. 5, during operation, the metering device 10 is positioned under an inverted first container 100 containing, for example, lyophilized powder. The piercing portion 42 of the metering device 10 is inserted into the first container 100. At which point, the dispensing aid 80 is activated, drawing powder from the vial, through the piercing portion 42, and into the metering chamber 30. As discussed above, optionally, the volume of the metering chamber 30 can be adjusted to achieve a precise dose of powder by moving the metering member 60 within the metering chamber 30.

After removing the piercing portion 42 from the first container 100, the metering device 10 is positioned under an inverted second container 200 containing a reconstitution fluid. Optionally, the dispensing aid 80 can be removed from the metering device 10. The piercing portion 42 is then inserted into the second container 200 containing diluent, thereby causing fluid to flow into the metering chamber 30 and, thus, forming a reconstituted mixture.

Figure 3:
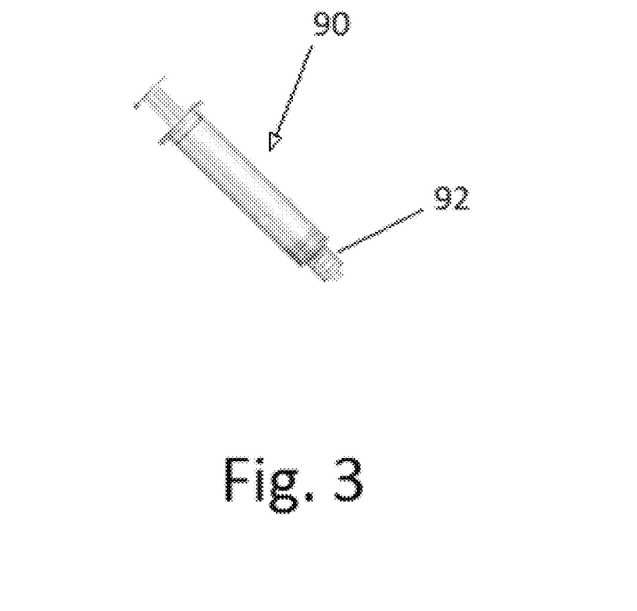
FIG. 3 depicts an exemplary extraction device according to the present disclosure.

The plug 70 is then removed from the extraction portion 50, and the mixture is extracted from the metering chamber 30 through the port 52 by, for example, an extraction device 90. The extraction device 90, now in receipt of the reconstituted mixture, is then ready for injection into a patient. According to the exemplary embodiment shown in FIG. 3 and FIG. 5, the extraction device 90 is a syringe, but other extracting means can be employed. In the exemplary embodiment, the syringe has a luer tip 92 for engagement with the port 52.

Although the exemplary embodiment of the present invention shown in FIG. 5 depicts use of the metering device 10 to mix one powder with one reconstituted fluid, other uses have been contemplated. For example, in accordance with the present invention, the metering device 10 could be used to combine any combination of two or more powders with one or more reconstitution fluids.

References to powder should be understood to include any particle based substance, including, for example, flakes, spheres, or rods.

While the foregoing drawings and descriptions set forth functional aspects of the disclosed systems, no particular arrangement of these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

Further, while embodiments of the present disclosure have been disclosed in connection with the preferred embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

What is claimed is:

1. A medical metering device, comprising:
   a housing containing a metering chamber defining a volume, said housing further having a connection portion, an extraction portion and a metering member, wherein the connection portion, extraction portion and metering member are in fluid communication with the metering chamber;
   wherein the connection portion is configured to direct powder and fluid into said metering chamber;
   wherein the metering member is configured to define the volume of the metering chamber; and
   a dispensing aid to facilitate removal of powder from a first container into the metering chamber via the connection portion.

2. The metering device of claim 1, wherein the connection portion comprises a needle.

3. The metering device of claim 2, wherein the dispensing aid is removably attachable to the connection portion, wherein the dispensing aid allows powder from the first container to enter the metering chamber through the needle.

4. The metering device of claim 1, wherein the extraction portion is configured to permit withdrawal of fluid from the metering chamber.

5. The metering device of claim 4, wherein the extraction portion comprises a port configured to receive an extraction device for withdrawing fluid from the metering chamber.

6. The metering device of claim 5, wherein the extraction device is a syringe.

7. The metering device of claim 5, a closure being removably attachable to the port.

8. The metering device of claim 1, wherein the metering member comprises one of a movable stopper, piston-rod mechanism, or a clamp in the metering chamber.

9. The metering device of claim 1, wherein the dispensing aid is configured to simultaneously receive an open end of the first container and the connection portion.

10. The metering device of claim 1, wherein the dispensing aid comprises one of either a vibration mechanism, a vacuum mechanism, or a pressure mechanism.

11. A medical metering device, comprising:
a housing containing a metering chamber, said housing further having a connection portion, an extraction portion and a metering member, wherein the connection portion, extraction portion and metering member are in fluid communication with the metering chamber;
the connection portion configured to direct powder and fluid into said metering chamber;
wherein the metering member is configured to define a volume of the metering chamber;
a dispensing aid removably attachable to the connection portion to facilitate removal of powder from a first container into the metering chamber, wherein the connection portion is further configured to facilitate removal of fluid from a second container into the metering chamber.

12. The metering device of claim 11, wherein the extraction portion is configured to permit withdrawal of fluid from the metering chamber.

13. The metering device of claim 12, wherein the extraction portion comprises a port configured to receive an extraction device for withdrawing fluid from the metering chamber.

14. The metering device of claim 13, wherein the extraction device is a syringe.

15. The metering device of claim 13, a closure being removably attachable to the port.

16. The metering device of claim 11, wherein the metering member comprises one of a movable stopper, piston-rod mechanism, or a clamp in the metering chamber.

17. The metering device of claim 11, wherein the connection portion comprises a needle.

18. The metering device of claim 11, wherein the dispensing aid is configured to simultaneously receive an open end of the first container and the connection portion.

19. The metering device of claim 11, wherein the dispensing aid comprises one of either a vibration mechanism, a vacuum mechanism, or a pressure mechanism.

20. A method of using a medical metering device, comprising:
providing a medical metering device, the device comprising:
a housing containing a metering chamber, said housing further having a connection portion, an extraction portion and a metering member, wherein the connection portion, extraction portion and metering member are in fluid communication with the metering chamber;
wherein the connection portion comprises a withdrawal member;
wherein the extraction portion comprises a port; and
a dispensing aid adjacent to the connection portion;
inserting the withdrawal member into a first container containing powder;
activating the dispensing aid to withdraw powder from the first container into the metering chamber via the withdrawal member;
removing the withdrawal member from the first container;
inserting the withdrawal member into a second container containing fluid;
drawing fluid into the metering chamber via the withdrawal member, thereby allowing a mixture to form in the metering chamber; and
removing the mixture from the metering chamber through the port.

* * * * *